United States Patent [19]

Kauffman et al.

[11] Patent Number: 5,270,047

[45] Date of Patent: Dec. 14, 1993

[54] LOCAL DELIVERY OF DIPYRIDAMOLE FOR THE TREATMENT OF PROLIFERATIVE DISEASES

[76] Inventors: Raymond F. Kauffman, 11420 Saint Andrews La.; Jai P. Singh, 13774 Hill Crest Ct., all of Carmel, Ind. 46032

[21] Appl. No.: 795,434

[22] Filed: Nov. 21, 1991

[51] Int. Cl.$^5$ .......................... A61F 2/02; A61K 9/14; A61K 31/74; A61K 37/22
[52] U.S. Cl. .................................. 424/422; 424/423; 424/424; 424/425; 424/426; 424/450; 424/484; 424/489; 424/78.08
[58] Field of Search ............... 424/422, 423, 424, 425, 424/426, 450, 484, 489, 78.08

[56] References Cited

U.S. PATENT DOCUMENTS 4,824,436 4/1989 Wolinsky ............................... 604/53

FOREIGN PATENT DOCUMENTS

383429A2 8/1990 European Pat. Off. .

OTHER PUBLICATIONS

Takehara, et al., "Dipyridamole Decreases Platelet-Derived Growth Factor Levels in Human Serum", *Arteriosclerosis*, 7, No. 2, 152-158 (1987).
Landymore, et al., "The Effects of Aspirin and Dipyridamole on Platelet Function and Prevention of Intimal Hyperplasia in Autologous Vein Grafts", *The Canadian Journal of Cardiology*, 4, No. 4, 56-59 (1988).
Ingermann-Wojenski, et al., "Model System to Study Interaction of Platelets with Damaged Arterial Wall", *Experimental and Molecular Pathology*, 48, No. 1, 116-134 (1988).
Lindblad, et al., "Effect of Anticoagulant and Antiplatelet Drugs on In Vitro Smooth Muscle Proliferation", *Artery*, 15, No. 4, 225-233 (1988).
Hagen, et al., "Antiplatelet Therapy Reduces Aortic Intimal Hyperplasia Distal to Small Diameter ascular Prostheses (PTFE) in NonHuman Primates", *Annals of Surgery*, 195, No. 3, 328-339, (1992).
Radic et al., "The role of aspirin and dipyramidole on vascular DNA synthesis and intimal hyperplasia following deendothialization", J. Surg. Res., 41(1), 84-91, 1986. (Abstract only).
Harker, et al., *Arteriosclerosis* 10: 828a (Sep. 1990).
Schwartz, et al., *The New England Journal of Medicine* 318: 1714-1719 (Jun., 1988).
Hermans, et al., *American Heart Journal* 122: 171-187 (Jul. 1991).
Faxon, et al., *The American Journal of Cardiology* 53: 72c-76c (Jul. 1984).
Bankhead, *Medical World News:* 26—34 (Feb. 1991).
Sanz, et al., *Circulation* 82: 765-773 (Sep. 1990).
Beckett, et al., *Arthritis and Rheumatism* 27: 1137-1143 (Oct. 1984).

*Primary Examiner*—Thurman K. Page
*Assistant Examiner*—Carlos Azpuru

[57] ABSTRACT

A method of inhibiting cell proliferation in mammals which comprises the local delivery of an inhibitory amount of dipyridamole. Inhibiting cell proliferation is useful for the treatment of proliferaive diseases such as vascular restonesis, scleroderma, psoriasis, and rheumatoid arthritis. This method includes the local delivery of dipyridamole to the proliferative site by various techniques including local delivery catheters, site specific carriers, implants, direct injection, or direct application.

9 Claims, No Drawings

LOCAL DELIVERY OF DIPYRIDAMOLE FOR THE TREATMENT OF PROLIFERATIVE DISEASES

BACKGROUND OF THE INVENTION

Proliferative diseases such as vascular restenosis, scleroderma, psoriasis, and rheumatoid arthritis share the fundamental mechanism of excessive proliferation of cells in a specific tissue or organ. In each of these diseases, the excessive proliferation of cells contributes significantly to the pathogenesis of the disease.

For example, the excessive proliferation of vascular smooth muscle cells contributes to the reocclusion of coronary arteries following percutaneous transluminal coronary angioplasty (PTCA), atherectomy, laser angioplasty and arterial bypass graft surgery. See "Intimal Proliferation of Smooth Muscle Cells as an Explanation for Recurrent Coronary Artery Stenosis after Percutaneous Transluminal Coronary Angioplasty," Austin et al., Journal of the American College of Cardiology 8:369-375 (August 1985).

Vascular restenosis remains a major long term complication following surgical intervention of blocked arteries by percutaneous transluminal coronary angioplasty (PTCA), atherectomy, laser angioplasty and arterial bypass graft surgery. In about 35% of the patients who undergo PTCA, reocclusion occurs within three to six months after the procedure. The current strategies for treating vascular restenosis include mechanical intervention by devices such as stents or pharmacologic therapies including heparin, low molecular weight heparin, coumarin, aspirin, fish oil, calcium antagonist, steroids, and prostacyclin. These strategies have failed to curb the reocclusion rate and have been ineffective for the treatment and prevention of vascular restenosis. See "Prevention of Restenosis after Percutaneous Transluminal Coronary Angioplasty: The Search for a 'Magic Bullet'," Hermans et al., American Heart Journal 122:171-187 (July 1991).

The excessive proliferation of fibroblast and mesenchymal cells is associated with rheumatoid arthritis and psoriasis. The inflammatory process that is characteristic of rheumatoid arthritis results in the release of growth factors that induce active proliferation of mesenchymal cells. This proliferation is associated with the production of excessive amounts of enzymes capable of destroying the connective tissues that comprise the joint. Pharmacologic agents that inhibit the proliferative response would be effective in repressing some of the destructive potential of rheumatoid arthritis. See "Recent Insights into the Pathogenesis of the Proliferative Lesion of Rheumatoid Arthritis," Harris, Arthritis and Rheumatism 19:68-72 (January-February 1976).

Scleroderma (systemic sclerosis) is a multisystem disease affecting primarily the vascular, cutaneous, musculoskeletal, gastrointestinal, pulmonary, cardiac, and renal systems. The apparent diffuse clinical features of systemic sclerosis are thought to be linked by a distinctive vascular lesion in the various target organs. This vascular lesion has inflammatory, proliferative, and indurative phases and is clearly related to the proliferation of the fibroblast and cells capable of fibroblast activity. Controlling this mechanism of fibroblastic activation and proliferation may be useful in treating or preventing systemic sclerosis. See "Pathogenesis of Systemic Sclerosis: A Vascular Hypothesis," Campbell et al., Seminars in Arthritis and Rheumatism 4:351-368 (May, 1975).

In the pathogenesis of proliferative diseases, excessive cell proliferation occurs as a result of the presence of various growth factors and cytokines such as platelet-derived growth factor (PDGF), epidermal growth factor (EGF), fibroblast growth factor (FGF) and interleukin-1 (IL-1). For example, growth factors produced by cellular constituents in the blood and the damaged arterial vessel wall mediate the proliferation of smooth muscle cells in vascular restenosis. A novel method of administering dipyridamole to inhibit cellular proliferation caused by various growth factors is therefore useful for the treatment of proliferative diseases such as psoriasis, rheumatoid arthritis, scleroderma, and vascular restenosis. The American Journal of Medicine 70:1231-1236 (June 1981).

Dipyridamole is commonly prescribed as an antiplatelet or phosphodiesterase inhibitor. It has been studied independently or in conjunction with aspirin and/or prostacyclin for the treatment of vascular restenosis. The results of these studies have demonstrated that dipyridamole, when systemically administered, is ineffective in treating or preventing vascular restenosis in patients. Hermans et al., American Heart Journal 122:171-187 (July, 1991); Harker et al., Arteriosclerosis 10:828a (September-October, 1990); and FitzGerald, The New England Journal of Medicine 316:1247-57 (May, 1987).

The present invention provides for the use of dipyridamole as an antiproliferative agent. The invention discloses the local delivery of dipyridamole as a method of inhibiting cell proliferation and is useful for the treatment of proliferative diseases such as restenosis, scleroderma, psoriasis, and rheumatoid arthritis.

SUMMARY OF THE INVENTION

This invention provides a method of inhibiting cell proliferation in mammals which comprises the local delivery of an inhibitory amount of dipyridamole.

DETAILED DESCRIPTION OF THE INVENTION

Dipyridamole is a well known compound used extensively as a coronary vasodilator. The Merck Index Tenth Edition: 3366 (1983). Its chemical name is 2,6-bis(diethanolamino)-4,8-dipiperidinopyrimido[5,4-d]pyrimidine. Its preparation is disclosed in British patent 807,826 (1959 to Thomae).

The local delivery of inhibitory amount of dipyridamole for the treatment of cell proliferation can be by a variety of techniques which administer the dipyridamole at or near the proliferative site. Examples of local delivery techniques are not intended to be limiting but to be illustrative of the techniques available. Examples include local delivery catheters, site specific carriers, implants, direct injection, or direct applications.

Local delivery by a catheter allows the administration of a pharmaceutical agent directly to the proliferative lesion. Examples of local delivery using a balloon catheter are described in EPO 383 492 A2 and U.S. Pat. No. 4,636,195 (Wolinsky, Jan. 13, 1987).

Local delivery by an implant describes the surgical placement of a matrix that contains the pharmaceutical agent into the proliferative lesion. The implanted matrix releases the pharmaceutical agent by diffusion, chemical reaction, or solvent activators. Langer, Science 249:1527-1533 (September, 1990).

An example of local delivery by an implant is the use of a stent. Stents are designed to mechanically prevent the collapse and reocclusion of the coronary arteries. Incorporating a pharmaceutical agent into the stent delivers the drug directly to the proliferative site. Local delivery by this technique is described in Kohn, *Pharmaceutical Technology* (October, 1990).

A second example is a delivery system in which a polymer that contains the pharmaceutical agent is injected into the lesion in liquid form. The polymer then cures to form the implant in situ. This technique is described in PCT WO 90/03768 (Donn, Apr. 19, 1990).

Another example is the delivery of a pharmaceutical agent by polymeric endoluminal sealing. This technique uses a catheter to apply a polymeric implant to the interior surface of the lumen. The pharmaceutical agent incorporated into the biodegradable polymer implant is thereby released at the surgical site. It is described in PCT WO 90/01969 (Schindler, Aug. 23, 1989).

A final example of local delivery by an implant is by direct injection of vesicles or microparticulates into the proliferative site. These microparticulates may be composed of substances such as proteins, lipids, carbohydrates or synthetic polymers. These microparticulates have the pharmaceutical agent incorporated throughout the microparticle or over the microparticle as a coating. Delivery systems incorporating microparticulates are described in Lange, *Science* 249: 1527–1533 (September, 1990) and Mathiowitz, et al., *J. App. Poly. Sci.*, 26:809 (1981).

Local delivery by site specific carriers describes attaching the pharmaceutical agent to a carrier which will direct the drug to the proliferative lesion. Examples of this delivery technique includes the use of carriers such as a protein ligand or a monoclonal antibody. Lange, *Science* 249:1527–1533 (September, 1990).

Local delivery by direct application includes the use of topical applications. An example of a local delivery by direct application is applying the pharmaceutical agent directly to the arterial bypass graft during the surgical procedure.

Local delivery by direct injection describes injecting fine particles of dipyridamole suspended in an inert carrier such as sterile saline solution directly into the proliferative site.

The dosage of dipyridamole required to produce the inhibitory effect is dependent upon the local delivery technique used in administration. The preferred dosage range of an inhibitory amount of dipyridamole is defined to be about 1 µg/day to about 100,000 µg/day delivered at or near the proliferative site.

A critical aspect of the present invention provides for the local delivery of dipyridamole to prevent cell proliferation. Cellular proliferation may be induced by cytokines such as interleukin-1 (IL-1) or multiple growth factors such as platelet-derived growth factor (PDGF), epidermal growth factor (EGF), and/or fibroblast growth factor (FGF).

Previous attempts to use dipyridamole for the treatment of restenosis have been ineffective due to the systemic method of administration. Systemic administration includes delivery techniques that introduce the pharmaceutical agent to the entire organism. Examples of systemic delivery include oral and intravenous administration.

Serum reduces the effectiveness of systemically administered dipyridamole as an inhibitor of cell proliferation. The effect of serum on the antiproliferative activity of dipyridamole was demonstrated as follows: Smooth muscle cells from rabbit aorta (derived by explant method as described in Ross, *Journal of Cell Biology* 50:172 (1971)) were seeded in 96 well tissue culture plates in Dulbecco's Modified Eagle's Medium (DMEM) containing 10% fetal bovine serum (Gibco Laboratories, Grand Island, N.Y.), 2 mM L-glutamine, 100 U/ml penicillin, and 100 µg/ml streptomycin. Growth arrested, confluent cultures in 96 well microtiter plates were incubated in medium containing 1%, 5% or 20% serum (Hyclone Laboratories, Logan, Utah), 2 mM L-glutamine, 100 U/ml penicillin, 100 µg/ml streptomycin, 40 ng/ml PDGF (Genzyme, Cambridge, Mass.), 1 µci/ml $^3$H thymidine (DuPont, Boston, Mass.) and indicated concentrations of dipyridamole (Sigma Chemical, St. Louis, Mo.). Cells were incubated at 37° C. for 24 hours under 5% $CO_2$/95% air. At the end of 24 hours, cells were fixed in methanol and DNA synthesis was determined by $^3$H thymidine incorporation as described in Bonin et al., *Exp. Cell Res.* 181, 475–482 (1989). The following table demonstrates that increasing concentrations of serum attenuate the growth inhibitory effects of dipyridamole.

TABLE 1

Effect of serum concentration on inhibition of DNA synthesis by dipyridamole.

| Dipyridamole | % Inhibition of DNA Synthesis | | |
|---|---|---|---|
| (µg/ml) | 1% Serum | 5% Serum | 20% Serum |
| 0 | 0 | 0 | 0 |
| 0.04 | 59 | 52 | 6 |
| 0.08 | 70 | 53 | 0 |
| 0.15 | 79 | 60 | 33 |
| 0.3 | 80 | 71 | 38 |
| 0.6 | 86 | 80 | 60 |
| 1.2 | 90 | 87 | 74 |
| 2.5 | 93 | 92 | 77 |

The effect of systemically administered dipyridamole upon cell proliferation was demonstrated as follows:

Balloon injury to the left common carotid arteries of male Sprague-Dawley rats (350–400 g) was accomplished by three passes of an inflated 2F Fogarty balloon catheter (Baxter Healthcare, McGaw Park, Ill.) as described by Clowes et al., *Lab Invest.* 49:208-215 (1983). Animals were anesthetized with Ketamine (80 mg/kg, intramuscular, Aveco, Ft. Dodge, Iowa) and Rompun (16 mg/kg, intramuscular, Mobay Corp., Shawnee, Kans.). Entry of the balloon catheter to the left common carotid artery was made via a nick in the external carotid artery, which was tied off at the end of the surgical procedure. Dipyridamole was systemically administered for two weeks (0.03 and 0.10% wt/wt, as an admixture in the diet, equivalent to approximately 30 and 100 mg/kg/day, respectively). No significant effect upon intimal thickening in the balloon-injured rat carotid arteries was observed as demonstrated in Table 2.

TABLE 2

Effect of Systemic Administration of Dipyridamole Upon Intimal Thickening

| Systemic Administration of Dipyridamole (% in diet, wt/wt) | Area of Intimal Thickening $mm^2$, (% of control) |
|---|---|
| 0.00 | 0.120 ± 0.014 (100) |
| 0.03 | 0.116 ± 0.017 (97.6) |
| 0.10 | 0.109 ± 0.014 (90.8) |

The effect of the present invention to control the cellular proliferation and intimal thickening by the local delivery of dipyridamole has been demonstrated by in vivo studies. The following examples illustrate the present invention and are not intended to limit the same.

EXAMPLE 1

Balloon Injury of Carotid Arteries

Balloon injury to the left common carotid arteries of male Sprague-Dawley rats (350-400 g) was accomplished by three passes of an inflated 2F Fogarty balloon catheter as described by Clowes et al., *Lab Invest.* 49:208-215 (1983). Animals were anesthetized with Ketamine (80 mg/kg, intramuscular) and Rompun (16 mg/kg, intramuscular). Entry of the balloon catheter to the left common carotid artery was made via a nick in the external carotid artery, which was tied off at the end of the surgical procedure. Continuous local delivery of dipyridamole was accomplished by means of a minosmotic pump implanted subcutaneously in the back of the rat. Pumps were primed before surgery and implanted immediately following balloon injury. Dosing solutions were delivered to the adventitial (exterior) space surrounding the injured carotid artery via a microrenathane catheter (MRE-40, Baxter Healthcare, Santa Ana, Calif.) at a rate of 5 $\mu$l per hour. The catheter is sutured in place with two ligatures (4-0 silk) to the left external carotid artery.

Fourteen days post surgery, animals were anesthetized (vide supra) and perfused through the abdominal aorta in a retrograde manner at physiological pressure with a zinc formalin fixative (Anatech LTD., Battle Creek, Mich.). Middle sections (5 mm) of the carotids were removed from the animals, processed, and embedded in paraffin. Three adjacent cross sections (5 $\mu$m thick) of each vessel were cut, stained with hematoxylin and eosin, and cross-sectional intimal areas quantitated with an image analyzer (Quantimet 970, Cambridge Inst., Cambridge, UK).

The difference between intimal areas of drug-treated vs. control groups were analyzed for statistical significance using Student's t-test as described in Tallarida et al., *Manual of Pharmacologic Calculations with Computer Programs*, Springer-Verlag, New York, 1981, p. 51. P values less than 0.05 were taken to indicate statistical significance. The results are demonstrated in Table 3.

TABLE 3

| Effect of Local Administration of Dipyridamole Upon Intimal Thickening | |
|---|---|
| Local, Adventitial Administration of Dipyridamole ($\mu$g/day) | Area of Intimal Thickening mm$^2$, (% of control) |
| 0 (Vehicle) | 0.129 ± 0.013 (100) |
| 600 | 0.087 ± 0.011 (67.4)* |

*P < 0.05 vs. corresponding control group (i.e., absence of dipyridamole)

EXAMPLE 2

Dipyridamole also inhibits proliferation of cells of mesenchyme origin. Inhibition of fibroblast growth by dipyridamole is demonstrated as follows: 20,000 Balb/c3T3 fibroblasts (American Tissue Culture Type, CCL-163) were plated in 12 well tissue culture plates in 3 ml DMEM containing 5% fetal bovine serum, 2 mM L-glutamine, 100, U/ml penicillin, and 100 $\mu$g/ml streptomycin, and were incubated for 18-24 hours. Cells were then transferred to above medium containing indicated concentrations of dipyridamole. After three days cell growth was determined by counting using a ZM Coulter counter (Coulter Diagnostic, Inc.).

TABLE 4

| Inhibition of Fibroblast Growth by Dipyridamole | |
|---|---|
| Dipyridamole ($\mu$g/ml) | % Inhibition of Cell Growth |
| 0.0 | 0.0 |
| 1.0 | 0 |
| 5.0 | 55 |
| 10 | 72 |
| 20 | 86 |
| 40 | 95 |

EXAMPLE 3

Dipyridamole inhibits smooth muscle cell proliferation induced by multiple growth factors. Smooth muscle cells from rabbit aorta (derived by explant method) were seeded in 96 well tissue culture plates in DMEM containing 10% fetal bovine serum, 2 mM L-glutamine, 100 U/ml penicillin and 100 $\mu$g/ml streptomycin. Growth arrested, confluent cultures in 96 well microtiter plates were incubated in medium containing 1% platelet poor plasma, 2 mM L-glutanime, 100 U/ml penicillin, 100 $\mu$g/ml streptomycin, 20 ng/ml PDGF, 3 ng/ml EGF (Genzyme), 3 ng/ml FGF (Genzyme), 1 $\mu$ci/ml $^3$H thymidine and indicated concentrations of dipyridamole. Cells were incubated at 37° C. for 24 hours under 5% $CO_2$/95% air. At the end of 24 hours, cells were fixed in methanol. DNA synthesis was determined by $^3$H thymidine incorporation as previously described. The results in Table show that dipyridamole inhibits cell proliferation induced by PDGF, FGF, and EGF.

TABLE 5

| Inhibition of DNA Synthesis induced by PDGF, FGF or EGF by dipyridamole. | | | |
|---|---|---|---|
| Dipyridamole ($\mu$g/ml) | % Inhibition of DNA Synthesis | | |
| | FGF | EGF | PDGF |
| 0 | 0 | 0 | 0 |
| 0.08 | 67 | 68 | 64 |
| 0.15 | 74 | 76 | 71 |
| 0.32 | 80 | 85 | 82 |
| 0.64 | 87 | 90 | 89 |
| 1.2 | 92 | 94 | 93 |
| 2.5 | 93 | 96 | 96 |

We claim:

1. A method of inhibiting cell proliferation in mammals which comprises the local delivery of a therapeutic amount of dipyridamole sufficient to inhibit cell proliferation.

2. The method of use of claim 1 wherein the cells inhibited are vascular smooth muscle cells.

3. The method of use of claim 1 wherein the cells inhibited are fibroblast cells.

4. The method of use of claim 1 wherein the cells inhibited are mesenchymal cells.

5. The method of use of claim 1 where the local delivery is by means of direct application.

6. The method of use of claim 2 where the local delivery is by means of direct application.

7. The method of use of claim 3 where the local delivery is by means of direct application.

8. The method of use of claim 4 where the local delivery is by means of direct application.

9. A method of inhibiting cell proliferation in mammals which comprises the local delivery of a therapeutic amount of dipyridamole sufficient to inhibit cell proliferation wherein said cellular proliferation is induced by growth factors comprising platelet-derived growth factor (PDGF), epidermal growth factor (EGF), and/or fibroblast growth factor (FGF).

* * * * *